United States Patent
Inoue et al.

(10) Patent No.: US 8,039,425 B2
(45) Date of Patent: Oct. 18, 2011

(54) SKIN OR HAIR CLEANSER COMPOSITION COMPRISING AN ALKOXYLATED C8-C10 ALCOHOL AND A SILOXANE

(75) Inventors: Masaki Inoue, Wakayama (JP); Yasuhiro Doi, Wakayama (JP)

(73) Assignee: Kao Corporation, Tokyo (JP)

( * ) Notice: Subject to any disclaimer, the term of this patent is extended or adjusted under 35 U.S.C. 154(b) by 102 days.

(21) Appl. No.: 12/440,426

(22) PCT Filed: Sep. 7, 2007

(86) PCT No.: PCT/JP2007/000973
§ 371 (c)(1),
(2), (4) Date: Mar. 6, 2009

(87) PCT Pub. No.: WO2008/029516
PCT Pub. Date: Mar. 13, 2008

(65) Prior Publication Data
US 2010/0069276 A1   Mar. 18, 2010

(30) Foreign Application Priority Data

Sep. 8, 2006   (JP) ................................. 2006-244655

(51) Int. Cl.
*C11D 1/722* (2006.01)
*C11D 9/36* (2006.01)

(52) U.S. Cl. ........ 510/122; 510/119; 510/128; 510/130; 510/421; 510/422; 510/466

(58) Field of Classification Search .................. 510/119, 510/122, 130, 128, 421, 422, 466
See application file for complete search history.

(56) References Cited

U.S. PATENT DOCUMENTS

| | | | | |
|---|---|---|---|---|
| 4,311,608 | A | * | 1/1982 | Maurice ........................ 510/417 |
| 6,187,058 | B1 | * | 2/2001 | Massoni ........................... 8/406 |
| 6,486,109 | B1 | * | 11/2002 | Mondin ........................ 510/296 |
| 2003/0134760 | A1 | * | 7/2003 | Harrison et al. .............. 510/122 |
| 2003/0229948 | A1 | * | 12/2003 | Desenne et al. .................. 8/405 |

FOREIGN PATENT DOCUMENTS

| | | |
|---|---|---|
| CN | 1695592 A | 11/2005 |
| JP | 7-53991 A | 2/1995 |
| JP | 11-12594 A | 1/1999 |
| JP | 2002-308810 A | 10/2002 |
| JP | 2004-203801 A | 7/2004 |
| JP | 2004-277685 A | 10/2004 |
| JP | 2006-104267 A | 4/2006 |
| JP | 2007-211232 A | 8/2007 |

OTHER PUBLICATIONS

Office Action in Chinese Application No. 200780033127.1 mailed Oct. 13, 2010, including full English translation.

* cited by examiner

*Primary Examiner* — Charles Boyer
(74) *Attorney, Agent, or Firm* — Birch, Stewart, Kolasch & Birch, LLP

(57) ABSTRACT

Provided is a skin or hair cleanser composition having an excellent foaming property and making a good feeling upon use available from cleansing until after drying, which comprises:

from 0.2 to 20 wt. % of (A) a compound represented by the following formula (1):

$$R^1O\text{-}(AO)_n\text{-}R^2 \qquad (1)$$

wherein $R^1$ represents a straight-chain or branched alkyl or alkenyl group having from 8 to 10 carbon atoms, AO represents an alkyleneoxy group having from 2 to 4 carbon atoms, n is the number of the alkyleneoxy group and stands for a number from 0.5 to 3.5 on average, and $R^2$ represents a hydrogen atom or a methyl group, from 5 to 60 wt. % of (B) a surfactant other than the component (A), and from 0.1 to 10 wt. % of (C) at least one of silicones and monohydric alcohols having from 15 to 28 carbon atoms.

9 Claims, No Drawings

SKIN OR HAIR CLEANSER COMPOSITION COMPRISING AN ALKOXYLATED C8-C10 ALCOHOL AND A SILOXANE

FIELD OF THE INVENTION

The present invention relates to skin or hair cleanser compositions such as shampoo and body shampoo.

BACKGROUND OF THE INVENTION

Cleanser compositions are required to have various functions, such as emulsifying or solubilizing power acting on contaminants (e.g. oil) and cleansing power. Among them, a skin or hair cleanser composition, contrast to any industrial cleanser composition, is required to provide a good feeling upon use such as high foaming and good touch of foam during cleansing, good skin or hair sensation during rinsing or after drying, smooth finger combability or softness of the hair when it is applied to the hair, and easy rinsability or moisturized sensation on the skin after drying when it is applied to the hair. In order to meet such requirements, the skin or hair cleanser composition contains various silicones and oil ingredients. However, such ingredients cause many problems, when used in combination. For example, the performances of foam, such as foaming power and foam quality, worsen.

In order to improve the foaming property and viscosity adjustment of cleanser compositions, various foam boosters/thickening agents have been developed so far, and fatty acid alkanolamides, fatty acid amidopropylbetaines and the like are used as the general-purpose boosters/thickening agents. However, these nitrogen-containing compounds could invite the time-lapse change of color tone under some conditions. Specifically, fatty acid diethanolamide is suspected of carcinogenicity, where it is a nitroso compound. For these reasons, nitrogen-free thickening agents/foam boosters are in great demand.

Patent Document 1 describes, as a nitrogen-free thickening agent/foam booster, a cleanser composition excellent in foaming property, which composition is obtained using a monohydric alcohol having from 8 to 12 carbon atoms as a starting material and using, in combination therewith, a (poly) ethylene glycol alkyl ether with 1 to 3 moles of ethylene oxide and an anionic surfactant and/or an amphoteric surfactant.

Patent Documents 2 and 3 also describe an alkylene oxide adduct of a higher aliphatic alcohol having short-chain ethylene oxide or propylene oxide introduced therein and they show examples of improving a foaming property or low-temperature stability.

The compositions described in these patent documents, however, are not capable of satisfying a good feeling upon use, albeit with their foaming property. Moreover, these compositions have not been able to provide a sufficient feeling upon use required for skin or hair cleanser compositions.

As mentioned above, none of the prior documents describe a skin or hair cleanser composition that can meet requirements for an excellent foaming property and an excellent feeling upon use alike. Thus there has been a demand for the development of a skin or hair cleanser composition capable of satisfying both an excellent foaming property and a good feeling upon use from the outset of cleansing until after drying.

[Patent Document 1] JP-A-2004-277685
[Patent Document 2] JP-A-11-12594
[Patent Document 3] JP-A-07-53991

DISCLOSURE OF THE INVENTION

The present invention provides a hair or skin cleanser composition containing the following components (A), (B), and (C):
from 0.2 to 20 wt. % of (A) a compound represented by the following formula (1):

$$R^1O\text{-}(AO)_n\text{—}R^2 \tag{1}$$

wherein $R^1$ represents a straight-chain or branched alkyl or alkenyl group having from 8 to 10 carbon atoms, AO represents an alkyleneoxy group having from 2 to 4 carbon atoms, n is the number of the alkyleneoxy group and stands for a number from 0.5 to 3.5 on average, and $R^2$ represents a hydrogen atom or a methyl group,
from 5 to 60 wt. % of (B) a surfactant other than the component (A), and
from 0.1 to 10 wt. % of (C) at least one selected from silicones and monohydric alcohols having from 15 to 28 carbon atoms.

The present invention also provides a method of cleansing the skin or the hair, which includes applying the cleanser composition to the skin or hair.

The present invention further provides use of the cleanser composition for cleansing the skin or the hair.

DETAILED DESCRIPTION OF THE INVENTION

A purpose of the present invention is to provide a skin or hair cleanser composition having an excellent foaming property and providing a good feeling upon use from cleansing until after drying.

The present inventors have found that the skin or hair cleanser composition containing the above-described components (A), (B), and (C) has an excellent foaming property and providing an excellent feeling upon use.

The skin or hair cleanser composition of the present invention has an excellent foaming property and provides a good feeling upon use from cleansing until after drying.

In the formula (1) of the component (A), $R^1$ represents a straight-chain or branched alkyl or alkenyl group having from 8 to 10 carbon atoms. From the standpoint of reducing an odor, straight-chain alkyl groups are preferred. From the standpoint of a foaming property, $R^1$ has preferably 8 carbon atoms. When $R^1$ represents an alkyl mixture, the content of the alkyl group having 8 carbon atoms is preferably 50 wt. % or greater, more preferably 80 wt. % or greater, even more preferably 98 wt. % or greater.

In the formula (1) of the component (A), AO represents an alkyleneoxy group having from 2 to 4 carbon atoms, of which a propyleneoxy group (which will hereinafter be abbreviated as "PO") and/or an ethyleneoxy group (which will hereinafter be abbreviated as "EO") is preferred. POs and/or EOs may be added either in block or at random, but POs and/or EOs added in block are preferred. From the standpoint of reducing an odor, POs and EOs added in block in order of mention are more preferred and only POs added in block are even more preferred.

In the compound represented by the formula (1) of the component (A), n stands for a number from 0.5 to 3.5 on average. From the standpoint of foaming property and odor reduction, it stands for preferably from 1 to 3, more preferably from 2 to 3, even more preferably from 2 to 2.7.

In the formula (1), $R^2$ represents a hydrogen atom or a methyl group, with a hydrogen atom being preferred.

The skin or hair cleanser composition, if it contains the component (A) in an amount of from 0.2 to 20 wt. %, can have a sufficient foaming power without losing its feeling upon use or conditioning effect. The amount is preferably from 0.3 to 15 wt. %, more preferably from 0.5 to 10 wt. %.

The surfactant as the component (B) is at least one surfactant selected from the group consisting of surfactants other than the component (A), that is, anionic surfactants, nonionic surfactants other than the component (A), amphoteric surfactants, and cationic surfactants. The specific examples of the surfactants will be described hereinafter, but should not be construed as being limited thereto.

The anionic surfactants are preferably sulfate surfactants, sulfonate surfactants, carboxylate surfactants, phosphate surfactants, and amino acid surfactants. Examples include alkyl sulfates, polyoxyalkylene alkyl ether sulfates, polyoxyalkylene alkenyl ether sulfates, alkyl sulfosuccinates, polyoxyalkylene alkyl sulfosuccinates, polyoxyalkylene alkyl phenyl ether sulfates, alkane sulfonates, acyl isethionates, acyl methyltaurates, higher fatty acid salts, polyoxyalkylene alkyl ether acetates, alkyl phosphates, polyoxyalkylene alkyl ether phosphates, acyl glutamates, alanine derivatives, glycine derivatives, and arginine derivatives.

Of these, polyoxyethylene alkyl ether sulfates, polyoxyethylene alkenyl ether sulfates, alkyl sulfates, higher fatty acid salts, polyoxyalkylene alkyl ether acetates, alkyl phosphates, and polyoxyalkylene alkyl ether phosphates are preferred, with those represented by the following formula (2) or (3) being more preferred.

$$R^3\text{—}O(CH_2CH_2O)_pSO_3M \qquad (2)$$

$$R^4\text{—}OSO_3M \qquad (3)$$

wherein $R^3$ represents an alkyl or alkenyl group having from 10 to 18 carbon atoms, $R^4$ represents an alkyl group having from 10 to 18 carbon atoms, M represents an alkali metal, an alkaline earth metal, ammonium, an alkanolamine, or a basic amino acid, and p stands for the number of ethyleneoxy groups and is from 1 to 5 on average.

Examples of the nonionic surfactants include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers other than the component (A), polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides, and alkyl glycosides. Of these, polyoxyalkylene alkyl ethers other than the component (A), alkyl glycosides, polyoxyalkylene $C_8$-$C_{20}$ fatty acid esters, polyoxyethylene sorbitan fatty acid esters, polyoxyethylene hydrogenated castor oils, and fatty acid alkanolamides are preferred. As the polyoxyalkylene alkyl ethers other than the component (A), polyoxyethylene (the average number of moles of ethylene oxide added: from 5 to 26) alkyl (having from 12 to 20 carbon atoms) ethers, polyoxypropylene (the average number of moles of propylene oxide added: from 5 to 26) alkyl (having from 12 to 20 carbon atoms) ethers, and polyoxyethylene (the average number of moles of ethylene oxide added: from 5 to 26)/polyoxypropylene (the average number of moles of propylene oxide added: from 5 to 26) alkyl (having from 12 to 20 carbon atoms) ethers are preferred. As the alkyl glycosides, those having an alkyl group with from 8 to 14 carbon atoms and a condensation degree of sugar (glucose) of from 1 to 2 are preferred. They may be either monoalkanolamides or dialkanolamides, but those having a hydroxyalkyl group with 2 or 3 carbon atoms are preferred. Specific examples of the fatty acid alkanolamide include oleic diethanolamide, palm-kernel fatty acid diethanolamide, coconut fatty acid diethanolamide, lauric diethanolamide, polyoxyethylene coconut fatty acid monoethanolamide, coconut fatty acid monoethanolamide, lauric monoisopropanolamide, lauric monoethanolamide, palm-kernel fatty acid methyl ethanolamide, and coconut fatty acid methyl ethanolamide.

Examples of the amphoteric surfactants include betaine surfactants and amine oxide surfactants. Of these, betaine surfactants such as imidazoline betaines, alkyldimethylaminoacetic acid betaines, fatty acid amidopropylbetaines, and alkyl hydroxy sulfobetaines and amine oxide surfactants such as alkyl dimethyl amine oxides are more preferred, with alkylcarboxymethylhydroxyethyl imidazolium betaines, fatty acid amidopropyl betaines, alkyl hydroxy sulfobetaines, and alkyl dimethyl amine oxides being even more preferred. Fatty acid amidopropyl betaines and alkyl hydroxy sulfobetaines having an alkyl group with from 8 to 18 carbon atoms are preferred, of which those having an alkyl group with from 10 to 16 carbon atoms are more preferred. Of these, lauric amidopropyl betaine, palm-kernel fatty acid amidopropyl betaines, coconut fatty acid amidopropyl betaines and lauryl hydroxy sulfobetaine are even more preferred. Alkyl dimethyl amine oxides having an alkyl group with from 8 to 18 carbon atoms are preferred, with those having an alkyl group with from 10 to 16 carbon atoms being more preferred. Of these, lauryl dimethyl amine oxide and myristyl dimethyl amine oxide are even more preferred.

Examples of the cationic surfactants include quaternary ammonium salts described in JP-A-2000-178146 and represented by the following formula (4):

$$R^5\text{—}\underset{\underset{R^8}{|}}{\overset{\overset{R^6}{|}}{N^+}}\text{—}R^7 \quad Z^- \qquad (4)$$

wherein at least one of $R^5$, $R^6$, $R^7$, and $R^8$ represents a straight-chain or branched alkyl or alkenyl group which may be substituted with an alkoxy group having from 12 to 28 carbon atoms in total, preferably a straight-chain or branched alkoxy group, preferably from 16 to 28 carbon atoms, an alkenyloxy group, an alkanoylamino group, an alkenoylamino group, an alkanoyl group, or an alkanoyloxy group, while the remaining group(s) each represents a benzyl group, an alkyl group having from 1 to 5 carbon atoms, a hydroxyalkyl group, or a polyoxyethylene group having ethylene oxide added in the total number of moles of 10 or less, and $Z^-$ represents a halogen ion or an organic anion selected from, for example, acetate, citrate, lactate, glycolate, phosphate, nitrate, sulfonate, sulfate, and alkyl sulfates.

Preferred examples of the compound (4) include compounds of the formula (4) in which at least one of $R^5$, $R^6$, $R^7$, and $R^8$ represents an alkyl group which may be substituted with an alkoxy group having in total 8 to 22 carbon atoms and the remaining group(s) each represents a methyl, ethyl or benzyl group. More preferred specific examples include mono(long-chain alkyl) trimethylammonium chlorides such as stearyl trimethylammonium chloride and octadecyloxypropyltrimethyl ammonium chloride and di(long-chain alkyl)dimethylammonium chlorides such as distearyldimethylammonium chloride and branched dialkyldimethylammonium chloride.

The surfactant as the component (B) is preferably at least one surfactant selected from the group consisting of the anionic surfactants, the nonionic surfactants, and the amphoteric surfactants from the standpoint of a foaming property.

The content of the component (B) in the skin or hair cleanser composition is preferably from 5 to 60 wt. %, more preferably from 8 to 40 wt. %, even more preferably from 10 to 30 wt. % from the standpoint of a foaming property and economy.

The component (A) and the component (B) are added at a (A)/(B) weight ratio of preferably from 0.005 to 1, more preferably from 0.01 to 1, even more preferably from 0.03 to 0.5 from the standpoint of a foaming property and economy.

The following are examples of the silicone to be used as the component (C).

(1) Dimethylpolysiloxane represented by the following formula:

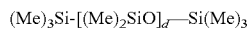

$(Me)_3Si-[(Me)_2SiO]_d-Si(Me)_3$ wherein Me represents a methyl group and d stands for a number from 3 to 20000.

(2) Branched polyglycerol-modified silicones described in JP-A-2005-97150, i.e., a branched polyglycerol-modified silicones wherein at least four (on average) glycerol groups or glycidol groups represented by the following structural formula (I), (II), (III), (IV), or (V):

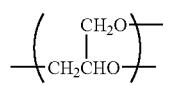 (I)

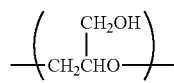 (II)

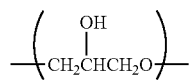 (III)

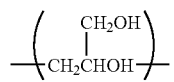 (IV)

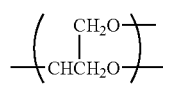 (V)

are the same or differently connected to one another, and wherein at least one branched polyglycerol chain containing at least one of the groups represented by the structural formulas (1) and (V) is connected to the silicon atom of a silicone via a linking group (e.g. "Sofcare GS-G", commercially available from Kao Corporation).

(3) Additional examples include polyether-modified silicones, amino-modified silicones, methylphenylpolysiloxane, fatty acid-modified silicones, and cyclic silicones.

Examples of the monohydric alcohol having from 15 to 28 carbon atoms to be used as the component (C) include cetyl alcohol, stearyl alcohol, behenyl alcohol, and octyl dodecanol. Of these, straight-chain monohydric alcohols having from 16 to 22 carbon atoms are preferred from the standpoint of a feeling of use.

As the component (C), one or more of them may be used in combination. The content of the component (C) in the entire skin or hair cleanser composition is preferably from 0.1 to 10 wt. %, more preferably from 0.3 to 8 wt. %, even more preferably from 0.5 to 5 wt. % from the standpoint of a foam quality, a touch feel, and conditioning effects.

The component (A) and the component (C) are added at an (A)/(C) weight ratio of preferably from 0.05 to 50, more preferably from 0.1 to 30, even more preferably form 0.2 to 20 from the standpoint of a foaming property and a touch feel.

The component (C) and the component (B) are added at a (C)/(B) weight ratio of preferably from 0.005 to 1, more preferably from 0.01 to 0.5, even more preferably from 0.02 to 0.25 from the standpoint of a foaming property and a touch feel.

The skin or hair cleanser composition of the present invention may contain further, as needed, glycerin, humectants, cationic polymers, polysaccharides, polypeptides, pearlescent agents, solvents, liquid-crystal forming bases, colorants, perfumes, propellants, chelating agents such as edetates or citrates, pH regulators, antiseptics, and anti-dandruffs. Examples of the cationic polymers include cationic celluloses and cationic polymers as described in JP-A-11-71435. Those of the antidandruff include zinc pyrithione and piroctone olamine.

Although the form of the skin or hair cleanser composition of the present invention is not particularly limited and the composition may be provided in a desired form such as liquid, foam, paste, cream, solid, or powder, it is provided preferably in liquid, paste, or cream form, more preferably in liquid form. When the composition is provided in liquid form, water, polyethylene glycol, or the like is used as a liquid medium. The amount of water is preferably from 10 to 80 wt. % in the entire composition.

The pH at 25° C. of the skin or hair cleanser composition of the present invention as a 20-fold diluted solution is preferably adjusted to from 4 to 10, more preferably from 5 to 9.

The skin or hair cleanser composition of the present invention can be produced in a manner known per se in the art and it can be provided, for example, as a hair shampoo or a body cleanser such as body shampoo, face wash, or hand soap.

EXAMPLES

Example 1

Hair shampoos shown in Table 3 were prepared in a manner known per se in the art by using alkylene glycol ethers 1 to 10, surfactants, and the like shown in Tables 1 and 2 and their foaming property, touch of foam, finger combability during rinsing, combability after drying, and softness of hair were evaluated in accordance with the following manner. The results are shown in Table 3.

The shampoo (1 g) was applied to 20 g of the bleached hair (20 cm) of a Japanese female. When the shampoo was foamed for 30 seconds, the foaming property, touch of foam, finger combability during rinsing, and combability and softness of hair after blow drying were evaluated by a panel of five experts in accordance with the following criteria:

1) Foaming Property
   4: It has an excellent foaming property.
   3: It has a good foaming property.
   2: It has a fair foaming property.
   1: It has a bad foaming property.

2) Touch of Foam
   4: Foam has a creamy quality and touch of foam is excellent.
   3: Foam has a fair quality and touch of foam is good.
   2: Foam has a fair quality and touch of foam is a little bad.
   1: Foam has a rough quality and touch of foam is bad.

3) Finger Combability During Rinsing
4: Excellent finger combability without friction between hair strands
3: Good finger combability with weak friction between hair strands.
2: Not smooth finger combability with friction between hair strands.
1: Bad finger combability with strong friction between hair strands.
4) Combability after Drying
4: The dried hair is very smooth and has good combability.
3: The dried hair is almost smooth, though it slightly prevents combing.
2: The dried hair sometimes prevents combing.
1: The dried hair very often prevents combing and has therefore bad combability.
5) Softness of the Hair after Drying
4: Very soft and supple.
3: Soft
2: Slightly stiff.
1: Stiff.

In any evaluation, an average score of the five experts was calculated and the hair shampoo having a score of 3.5 or greater was evaluated as A, that having a score of 2.5 or greater but less than 3.5 was evaluated as B, that having a score of 1.5 or greater but less than 2.5 was evaluated as C, and that having a score of less than 1.5 was evaluated as D.

TABLE 1

| $R^1O\text{-}(AO)_n\text{-}R^2$ | $R^1$ | $R^2$ | $(AO)_n$ |
|---|---|---|---|
| Alkylene golycol ether 1 | n-octyl | H | $(PO)_{2.3}$ |
| Alkylene glycol ether 2 | n-octyl | H | $(EO)_2$ |
| Alkylene glycol ether 3 | 2-ethylhexyl | H | $(PO)_{2.5}$ |
| Alkylene glycol ether 4 | n-octyl/n-decyl (molar ratio: 1/1) | H | $(PO)_{1.8}$ |
| Alkylene glycol ether 5 | 2-ethylhexyl | H | $(EO)_1$ |
| Alkylene glycol ether 6 | n-octyl | H | $(PO)_{2.7}$ |
| Alkylene glycol ether 7 | n-octyl | H | $(EO)_3$ |

TABLE 2

| $R^1O\text{-}(AO)_n\text{-}R^2$ | $R^1$ | $R^2$ | $(AO)_n$ |
|---|---|---|---|
| Alkylene golycol ether 8 | n-dodecyl | H | $(EO)_2(PO)_2(EO)_3$ |
| Alkylene glycol ether 9 | n-decyl | H | $(PO)_1(EO)_6$ |
| Alkylene glycol ether 10 | n-propyl | H | $(PO)_2$ |

TABLE 3

| | Hair shampoo composition (wt. %) | Invention products | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| (A) | Alkylene golycol ether 1 | 3.0 | | | | | | | 0.5 | 8.0 | 5.0 | 2.0 | 3.0 | 3.0 |
| | Alkylene glycol ether 2 | | 1.0 | | | | | | | | | | | |
| | Alkylene glycol ether 3 | | | 1.0 | | | | | | | | | | |
| | Alkylene glycol ether 4 | | | | 1.0 | | | | | | | | | |
| | Alkylene glycol ether 5 | | | | | 1.0 | | | | | | | | |
| | Alkylene glycol ether 6 | | | | | | 1.0 | | | | | | | |
| | Alkylene glycol ether 7 | | | | | | | 1.0 | | | | | | |
| (A) Comparison | Alkylene glycol ether 8 | | | | | | | | | | | | | |
| | Alkylene glycol ether 9 | | | | | | | | | | | | | |
| | Alkylene glycol ether 10 | | | | | | | | | | | | | |
| (B) | Sodium polyoxyethylene (EOp = 2) alkyl ether sulfate | 17.0 | 14.0 | 10.0 | 15.0 | 15.0 | 15.0 | 15.0 | | 10.0 | 15.0 | | 17.0 | 17.0 |
| | Ammonium polyoxyethylene (EOp = 1) alkyl ether sulfate | | | | | | | | 13.0 | | | | | |
| | Alkyl polyglucoside [1] | | | 3.0 | | | | | | | | | | |
| | Alkylcarboxymethylhydroxyethyl imidazolinium betaine [2] | | | | | | | | | | | 10.0 | | |
| | Cetyl trimethyl ammonium chloride [3] | | | | | | | | | | | 1.0 | | |
| | Coconut fatty acid amidopropylbetaine | | | | | | | | 5.0 | | 0.5 | | | |
| | Lauryl dimethyl amine oxide | | | | | | | | | 2.0 | | | | |
| (C) | Dimethylpolysiloxane [4] | 3.0 | 2.0 | | | 2.0 | 2.0 | 2.0 | 2.0 | 2.0 | | 1.5 | | |
| | Polyglycerol-modified polydimethylsiloxane [5] | | 0.5 | | 0.5 | | | | 0.5 | | 0.5 | | | |
| | Polyether-modified silicone [6] | | | 0.2 | | | | | | | | | | |
| | Cetyl alcohol [7] | | 0.8 | 0.3 | 0.5 | 0.5 | 0.5 | | | | | 1.0 | | |
| | Behenyl alcohol [8] | | | | | | | | | | | | | 1.0 |
| | Ethanol | | | | | | | | | | | | | |
| | pH Regulator | q.s. | q.s. | q.s. | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance | Balance | Balance | Balance |
| Total | | 100 | 100 | 100 | 100 | 100 | 100 | 100 | 100 | 100 | 100 | 100 | 100 | 100 |
| pH (20-fold diluted solution, 25° C.) | | 6.5 | 6.5 | 6.2 | 7.2 | 6.5 | 6.6 | 6.3 | 5.1 | 6.0 | 6.0 | 6.8 | 6.1 | 5.5 |
| Evaluation results | Foaming property | A | A | B | B | A | A | B | A | A | B | B | A | A |
| | Touch of foam | A | A | A | B | A | A | A | A | A | A | A | A | A |
| | Finger combability during rinsing | B | B | A | A | B | A | A | A | B | A | A | A | A |
| | Combability after drying | A | A | A | B | A | A | A | A | B | A | A | A | A |
| | Softness after drying | A | A | A | A | A | A | A | A | A | A | B | B | B |

TABLE 3-continued

| Hair shampoo composition (wt. %) | | Comparative products | | | | | | | | | |
|---|---|---|---|---|---|---|---|---|---|---|---|
| | | 1 | 2 | 3 | 4 | 5 | 6 | 7 | 8 | 9 | 10 |
| (A) | Alkylene golycol ether 1 | | | | | | | 3.0 | 3.0 | 0.1 | 21.0 |
| | Alkylene glycol ether 2 | | | 1.0 | | | | | | | |
| | Alkylene glycol ether 3 | | | | | | | | | | |
| | Alkylene glycol ether 4 | | | | | | | | | | |
| | Alkylene glycol ether 5 | | | | | | | | | | |
| | Alkylene glycol ether 6 | | | | | | | | | | |
| | Alkylene glycol ether 7 | | | | | | | | | | |
| (A) Comparison | Alkylene glycol ether 8 | | | | 1.0 | | | | | | |
| | Alkylene glycol ether 9 | | | | | 8.0 | | | | | |
| | Alkylene glycol ether 10 | | | | | | 5.0 | | | | |
| (B) | Sodium polyoxyethylene (EOp = 2) alkyl ether sulfate | 17.0 | 17.0 | 14.0 | 18.0 | 10.0 | 15.0 | 17.0 | 17.0 | 17.0 | 17.0 |
| | Ammonium polyoxyethylene (EOp = 1) alkyl ether sulfate | | | | | | | | | | |
| | Alkyl polyglucoside [1] | | | | | | | | | | |
| | Alkylcarboxymethylhydroxyethyl imdazolinium betaine [2] | | | | | | | | | | |
| | Cetyl trimethyl ammonium chloride [3] | | | | | | | | | | |
| | Coconut fatty acid amidopropylbetaine | 3.0 | 3.0 | | | | | | | | |
| | Lauryl dimethyl amine oxide | | | | 7.0 | 2.0 | | | | | |
| (C) | Dimethylpolysiloxane [4] | | 3.0 | | | | | 0.05 | 12.0 | 3.0 | 3.0 |
| | Polyglycerol-modified polydimethylsiloxane [5] | | | | | | 0.5 | | | | |
| | Polyether-modified silicone [6] | | | | | | | | | | |
| | Cetyl alcohol [7] | | | | | | | | | | |
| | Behenyl alcohol [8] | | | | | | | | | | |
| | Ethanol | | | | | 5.0 | | | | | |
| | pH regulator | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance |
| Total | | 100 | 100 | 100 | 100 | 100 | 100 | 100 | 100 | 100 | 100 |
| pH (20-fold diluted solution, 25° C.) | | 6.5 | 6.5 | 6.5 | 7.0 | 7.0 | 6.0 | 6.5 | 6.5 | 6.5 | 6.5 |
| Evaluation results | Foaming property | C | D | A | B | B | C | A | D | D | D |
| | Touch of foam | C | C | C | C | D | B | C | C | C | C |
| | Finger combability during rinsing | C | B | D | C | D | B | C | D | B | D |
| | Combability after drying | C | B | D | D | D | C | D | B | B | B |
| | Softness after drying | C | B | D | D | D | B | D | B | B | B |

[1] "MYDOL 10" (product of Kao Corporation)
[2] "AMPHITOL 20YB" (product of Kao Corporation)
[3] "QUARTAMIN 60W" (product of Kao Corporation)
[4] "BY 22-050A" (product of Dow Corning Toray)
[5] "SOFCARE GS-G" (product of Kao Corporation)
[6] "KF-6012" (product of Shin-etsu Chemical)
[7] "KALCOL 6098" (product of Kao Corporation)
[8] "KALCOL 220-80" (product of Kao Corporation)

As shown in Table 3, Comparative Product 2 obtained by adding dimethylpolysiloxane to Comparative Product 1 prepared by the conventional technology has a weak foaming property and provides a slightly improved touch (known level). On the other hand, Comparative Product 3 containing a specific foam booster which is the component (A) of the present invention has a good foaming property but has a defect in touch. The touch feel drastically improves by addition of the component (C) (Invention Product 2).

Example 2

Body shampoos shown in Table 4 were prepared in a manner known per se in the art by using alkylene glycol ethers 1 to 7 shown in Tables 1 and 2, a surfactant, and the like and the foaming property, touch of foam, rinsability, and moisturized feel after drying were evaluated in the below-mentioned method. The results are shown in Table 4.

<Evaluation Method>

The foaming property, touch of foam, rinsability, and moisturized feel after drying when the body shampoo (1 g) was taken in hand and hands and arms were cleansed therewith were evaluated by a panel of five experts in accordance with the following criteria.

1) Foaming Property

4: Excellent foaming property

3: Good foaming property

2: Fair foaming property

1: Bad foaming property.

2) Touch of Foam

4: Foam has a creamy quality and touch of foam is excellent.

3: Foam has a fair quality and touch of foam is good.

2: Foam has a fair quality and touch of foam is a little bad.

1: Foam has a rough quality and touch of foam is bad.

3) Rinsability

4: Rinsability is excellent.

3: Rinsability is good.

2: Rinsability is slightly inferior and a slimy feel remains.
1: Rinsability is bad and a strong slimy feel remains.
5) Moisturized Feel after Drying
4: It provides a very moisturized feel.
3: It provides a moisturized feel.
2: It provides an insufficient moisturized feel.
1: It provides an excessively dry feel.

In any evaluation, an average score of the five experts was calculated and the body shampoo having a score of 3.5 or greater was evaluated as A, that having a score of 2.5 or greater but less than 3.5 was evaluated as B, that having a score of 1.5 or greater but less than 2.5 was evaluated as C, and that having a score of less than 1.5 was evaluated as D.

The results of Table 4 show that the invention product is remarkably improved by the synergistic effect of the combined use of a specific foam booster, a silicone and an oil bas, as is the hair shampoos shown in Table 3.

Example 3

A hair shampoo having the below-mentioned composition was prepared in a manner known per se in the art by using the alkylene glycol ether 1 and the like shown in Table 1.

TABLE 4

| | | Invention Product | | | | | | | | | Comparative product | | | | | |
|---|---|---|---|---|---|---|---|---|---|---|---|---|---|---|---|---|
| | Body shampoo composition (wt. %) | 14 | 15 | 16 | 17 | 18 | 19 | 20 | 21 | 22 | 11 | 12 | 13 | 14 | 15 | 16 |
| (A) | Alkylene golycol ether 1 | 2.0 | | | | | | | 8.0 | 5.0 | | | | | 2.0 | 2.0 |
| | Alkylene glycol ether 2 | | 2.0 | | | | | | | | | 2.0 | | | | |
| | Alkylene glycol ether 3 | | | 2.0 | | | | | | | | | | | | |
| | Alkylene glycol ether 4 | | | | 2.0 | | | | | | | | | | | |
| | Alkylene glycol ether 5 | | | | | 2.0 | | | | | | | | | | |
| | Alkylene glycol ether 6 | | | | | | 2.0 | | | | | | | | | |
| | Alkylene glycol ether 7 | | | | | | | 2.0 | | | | | | | | |
| (A) Comparison | Alkylene glycol ether 8 | | | | | | | | | | | | 1.0 | | | |
| | Alkylene glycol ether 9 | | | | | | | | | | | | | 8.0 | | |
| | Alkylene glycol ether 10 | | | | | | | | | | | | | | | |
| (B) | Sodium polyoxyethylene (EOp = 2) alkyl ether sulfate | 5.0 | 14.0 | | | | | | 10.0 | 15.0 | 14.0 | 14.0 | 18.0 | 10.0 | 1.0 | 13.0 |
| | Potassium alkylphosphate [1] | 20.0 | | 18.0 | | | | | | | | | | | 3.0 | 52.0 |
| | Potassium laurate | | | | 18.0 | 18.0 | 18.0 | 18.0 | | | | | | | | |
| | Coconut fatty acid amidopropylbetaine | | | | | | | | 1.0 | 2.0 | | | | | | |
| | Lauryl dimethyl amine oxide | | | | | | | | 2.0 | | | 7.0 | 2.0 | | | |
| (C) | Dimethylpolysiloxane [2] | 1.0 | | | 0.3 | 0.3 | 0.3 | 0.3 | | | | | | | 1.0 | 1.0 |
| | Polyglycerol-modified polydimethylsiloxane [3] | | 0.5 | | | | | | 0.5 | 0.5 | 0.5 | | | | | |
| | Polyether-modified silicone [4] | | | 0.5 | 0.1 | 0.1 | 0.1 | 0.1 | | | | | | | | |
| | Cetyl alcohol [5] | | | | | | | | 0.5 | | | | | | | |
| | Behenyl alcohol [6] | | | | | | | | | 0.5 | | | | | | |
| | Ethanol | | | | | | | | | | | | | 5.0 | | |
| | pH regulator | q.s. | q.s. | q.s. | q.s. | q.s. | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance | Balance | Balance | Balance | Balance | Balance |
| Total | | 100 | 100 | 100 | 100 | 100 | 100 | 100 | 100 | 100 | 100 | 100 | 100 | 100 | 100 | 100 |
| pH (diluted to 20-fold, 25° C.) | | 6.5 | 6.5 | 6.2 | 8.5 | 8.5 | 8.4 | 8.5 | 6.0 | 6.0 | 6.5 | 6.5 | 7.0 | 7.0 | 6.5 | 6.5 |
| Evaluation results | Foaming property | A | A | B | A | A | A | B | A | A | C | B | B | B | D | B |
| | Touch of foam | A | A | B | A | A | A | A | A | A | C | D | C | D | D | C |
| | Rinsability | A | A | A | A | A | A | A | A | A | C | C | C | C | C | C |
| | Moisturized feel after drying | A | A | B | B | B | A | B | A | A | A | D | D | D | A | C |

[1] "PRIOLY B-650D" (product of Kao Corporation)
[2] "BY 22-050A" (product of Dow Corning Toray)
[3] "SOFCARE GS-G" (product of Kao Corporation)
[4] "KF-6012" (product of Shin-etsu Chemical)
[5] "KALCOL 6098" (product of Kao Corporation)
[6] "KALCOL 220-80" (product of Kao Corporation)

| (Component) | (wt. %) |
|---|---|
| Alkylene glycol ether 1 | 0.7 |
| Ammonium polyoxyethylene (1) lauryl ether sulfate * | 12.0 |
| Lauric monoethanolamide | 0.8 |
| Silicone emulsion ** | 2.0 |
| Cationic polymer *** | 0.2 |
| Perfume, methyl paraben | q.s. |
| Purified water | Balance |
| Total | 100.0 |

* "EMAL 125A" (product of Kao Corporation)
** "BY22-060" (product of Dow Corning Toray)
*** "POIZ C-150L" (product of Kao Corporation)

The hair shampoo thus obtained had a good foaming property and permitted smooth finger combability from cleansing until after drying and thus provided an excellent feeling upon use.

Example 4

A shampoo having the below-mentioned composition was prepared in a manner known per se in the art by using the alkylene glycol ether 1 and the like shown in Table 1.

| (Component) | (wt. %) |
|---|---|
| Alkylene glycol ether 1 | 0.5 |
| Sodium polyoxyethylene (3) lauryl ether sulfate * | 15.0 |
| Polyglycerol-modified polydimethylsiloxane ** | 0.5 |
| Lauryl hydroxy sulfobetaine *** | 2.0 |
| Glycerin | 3.0 |
| Perfume, methyl paraben | q.s. |
| Purified water | Balance |
| Total | 100.0 |

* "EMAL 327" (product of Kao Corporation)
** "SOFCARE GS-G" (product of Kao Corporation)
*** "AMPHITOL 20HD" (product of Kao Corporation)

The hair shampoo thus obtained had a good foaming property and permitted smooth finger combability from cleansing until after drying and thus provided an excellent feeling upon use.

Example 5

A body shampoo having the below-mentioned composition was prepared in a manner known per se in the art by using the alkylene glycol ether 2 and the like shown in Table 1.

| (Component) | (wt. %) |
|---|---|
| Alkylene glycol ether 2 | 2.0 |
| Lauryl phosphate * | 30.0 |
| Polyglycerol-modified polydimethylsiloxane ** | 0.5 |
| Amidopropylbetaine *** | 2.0 |
| Glycerin | 3.0 |
| Perfume, methyl paraben | q.s. |
| Purified water | Balance |
| Total | 100.0 |

* "PRIIOLY B-650D" (product of Kao Corporation)
** "SOFCARE GS-G" (product of Kao Corporation)
*** "AMPHITOL 20HD" (product of Kao Corporation)

The body shampoo thus obtained had a good foaming property, provided foam with a good foam quality during cleansing, left a moisturized feel to the skin even after drying, and thus had an excellent feeling upon use.

Example 6

A face wash having the below-mentioned composition was prepared in a manner known per se in the art by using the alkylene glycol ether 2 and the like shown in Table 1.

| (Component) | (wt. %) |
|---|---|
| Lauryl phosphate * | 45.0 |
| Sodium polyoxyethylene (2) lauryl ether sulfate ** | 5.0 |
| Alkylene glycol ether 2 | 5.4 |
| Lauryl hydroxy sulfobetaine *** | 5.0 |
| Glycerin | 1.0 |
| Sorbitol | 2.0 |
| Polyglycerol-modified polydimethylsiloxane **** | 0.6 |
| Perfume, methyl paraben | q.s. |
| Purified water | Balance |
| Total | 100.0 |

* "PRIOLY B-650D" (product of Kao Corporation)
** "EMAL 227" (product of Kao Corporation)
*** "AMPHITOL 20HD" (product of Kao Corporation)
**** "SOFCARE GS-G" (product of Kao Corporation)

The invention claimed is:

1. A method of cleansing the skin or hair, which comprises applying a hair or skin cleanser composition to the skin or hair;
   wherein the cleanser composition comprises the following components (A), (B), and (C):
   from 0.3 to 20 wt. % of (A) a compound represented by the following formula (I):

$$R^1O\text{-}(AO)_n\text{---}R^2 \qquad (1)$$

wherein $R^1$ represents a straight-chain or branched alkyl or alkenyl group having from 8 to 10 carbon atoms, AO represents an alkyleneoxy group having from 2 to 4 carbon atoms, n is the number of alkyleneoxy groups and stands for a number from 0.5 to 3.5 on average, and $R^2$ represents a hydrogen atom or a methyl group,
   from 5 to 30 wt. % of (B) a surfactant other than the component (A), and
   from 0.1 to 10 wt. % of (C) at least one selected from the group consisting of:
   (1) a dimethylpolysiloxane represented by the following formula:

$$(Me)_3Si\text{---}[(Me)_2SiO]_d\text{---}Si(Me)_3$$

wherein Me represents a methyl group and d stands for a number from 3 to 20000,
   (2) a branched polyglycerol-modified silicone,
   (3) a polyether-modified silicone,
   (4) an amino-modified silicone,
   (5) methylphenylpolysioxane,
   (6) a fatty acid-modified silicone, and
   (7) a cyclic silicone;
   wherein the component (A) and the component (B) are added at an (A)/(B) weight ratio of from 0.01 to 1.

2. The method of cleansing the skin or hair according to claim 1, wherein the content of the component (A) is from 0.3 to 10 wt. %.

3. The method of cleansing the skin or hair according to claim 1, wherein the content of the component (B) is from 10 to 30 wt. %.

4. The method of cleansing the skin or hair according to claim 1, wherein the component (A) and the component (C) are added at an (A)/(C) weight ratio of from 0.05 to 50.

5. The method of cleansing the skin or hair according to claim 1 or 4, wherein the component (C) and the component (B) are added at a (C)/(B) weight ratio of from 0.005 to 1.

6. The method of cleansing the skin or hair according to claim 1, wherein the component (B) is at least one surfactant selected from the group consisting of anionic surfactants, nonionic surfactants and amphoteric surfactants.

7. The method of cleansing the skin or hair according to claim 1, wherein n in the formula (I) representing the component (A) stands for a number from 1 to 3.

8. The method of cleansing the skin or hair according to claim 1, wherein AO is a propyleneoxy group.

9. The method of cleansing the skin or hair according to claim 1, wherein the component (B) is an anionic surfactant.

* * * * *

UNITED STATES PATENT AND TRADEMARK OFFICE
CERTIFICATE OF CORRECTION

| | | |
|---|---|---|
| PATENT NO. | : 8,039,425 B2 | Page 1 of 1 |
| APPLICATION NO. | : 12/440426 | |
| DATED | : October 18, 2011 | |
| INVENTOR(S) | : Masaki Inoue et al. | |

It is certified that error appears in the above-identified patent and that said Letters Patent is hereby corrected as shown below:

IN THE CLAIMS:

Claim 1, at column 14, line 35, change "formula (I)" to --formula (1)--.

Claim 7, at column 16, line 2, change "formula (I)" to --formula (1)--.

Signed and Sealed this
Sixth Day of March, 2012

David J. Kappos
*Director of the United States Patent and Trademark Office*